United States Patent [19]

Kitahata et al.

[11] Patent Number: 5,366,879
[45] Date of Patent: Nov. 22, 1994

[54] METHOD OF PREPARING BRANCHED CYCLODEXTRIN

[75] Inventors: Sumio Kitahata, 621-440, Noda, Kumatori-cho, Sennan-gun, Osaka; Koji Hara, Yokohama; Koki Fujita, Yokohama; Nobuhiro Kuwahara, Yokohama; Hirofumi Nakano, 14-3, 3-chome, Hattorinishi-machi, Toyonaka-shi, Osaka, all of Japan

[73] Assignees: Ensuiko Sugar Refining Co., Ltd., Yokohama; Sumio Kitahata; Hirofumi Nakano, both of Osaka, all of Japan

[21] Appl. No.: 992,862

[22] Filed: Dec. 17, 1992

[30] Foreign Application Priority Data

Apr. 8, 1992 [JP] Japan .................. 4-114303

[51] Int. Cl.$^5$ .................. C12P 19/18; C12P 19/16; C12P 19/22
[52] U.S. Cl. .................. 435/101; 435/98; 536/124; 536/103
[58] Field of Search .................. 435/101, 98; 536/124, 536/103

[56] References Cited

U.S. PATENT DOCUMENTS 4,871,840 10/1989 Kobayashi .................. 536/103
4,910,137 3/1990 Kobayashi .................. 536/103

FOREIGN PATENT DOCUMENTS 2193963 2/1988 United Kingdom .

OTHER PUBLICATIONS

Patent Abstracts of Japan, vol. 11, No. 184, p. 92 C 427, Jun. 12, 1987 of JP 62-6696.
Patent Abstracts of Japan, vol. 11, No. 176, p. 114 C 426, Jun. 5, 1987 of JP 62-3795.

*Primary Examiner*—Ronald W. Griffin
*Attorney, Agent, or Firm*—Frishauf, Holtz, Goodman & Woodward

[57] ABSTRACT

Disclosed is a method of producing a branched cyclodextrin where a liquid containing a cyclodextrin and a branched oligosaccharide is treated with a debranching enzyme. By the method, a branched cyclodextrin having a maltosyl or maltotriosyl group as bonded to the glucose of a CD molecule via an $\alpha$-1,6 bond is obtained efficiently.

11 Claims, 4 Drawing Sheets

(I)

(I)

(III)

(IV)

(V)

(VI)

G : Glucosyl residue

METHOD OF PREPARING BRANCHED CYCLODEXTRIN

FIELD OF THE INVENTION

The present invention relates to a method of preparing a branched cyclodextrin and, more precisely, to that in which a cyclodextrin is treated with a debranching enzyme along with a branched oligosaccharide as a glycosyl donor due to the transglycosylation activity of the enzyme.

BACKGROUND OF THE INVENTION

A cyclodextrin (hereinafter referred to as "CD") is a cyclic dextrin composed of glucoses bonded to each other by an $\alpha$-1,4 bond therebetween, and $\alpha$-, $\beta$- and $\gamma$-CD each comprising 6,7 and 8 glucoses, respectively, are well known.

These CDs have cavities in the inside of the molecule and the inside of the cavities is hydrophobic. Therefore, these have an including capacity for forming inclusion (clathrate) compounds, taking various oily substances thereinto. Accordingly, utilizing the property of them, various uses of CDs for ① stabilization of unstable substances, ② possession of volatile substances, ③ masking of offensive odor and ④ solubilization of hardly soluble or insoluble substances are taken into consideration.

However, $\alpha$-CD and $\beta$-CD have a drawback that they nave a low solubility (about several % or less) at a low temperature. In order to overcome the drawback, recently, branched CDs have been developed. Branched CDs have a constitution where a glucosyl group, a maltosyl group or a maltooligosyl group is bonded to the glucose in the CD molecule via an $\alpha$-1,6 bond, and they are extremely highly soluble in water and have other various characteristics, being different from non-branched CDs.

For preparing such branched CDs, some methods have heretofore been proposed. Of them, a method which is being utilized most often industrially at present is such that a branched CD is obtained from a high concentration of maltose and the CD is produced by a condensation reaction with pullulanase. In accordance with the method, a maltosyl-CD is produced at a fairly high yield but at the same time a dimaltosyl-CD having an additional maltose of one molecule is bonded to another glycosyl group of a maltosyl-CD via an $\alpha$-1,6 bond is also produced. Therefore for the purpose of isolating only a maltosyl-CD from the reaction mixture, much cost and much time are disadvantageously necessary.

Taking the above-mentioned characteristics of branched CDs into consideration, the present inventors variously investigated for the purpose of efficiently producing maltosyl-CDs. As a result, they have completed a method of producing branched CDs by bonding an $\alpha$-maltosyl group to the glucosyl group of an $\alpha$-, $\beta$- or $\gamma$-CD from a branched oligosaccharide by transglycosylation of a debranching enzyme.

In addition, they further have found that an isoamylase derived from Pseudomonas amylodelamosa is used for efficiently producing a maltosyl-CD or maltotriosyl-CD having one molecule of maltosyl group or maltotriosyl group as bonded to the glucosyl group of $\alpha$-, $\beta$- or $\gamma$-CD via $\alpha$-1,6-bond therebetween by transglycosylation. On the basis of the finding, they have completed the present invention.

SUMMARY OF THE INVENTION

Specifically, the present invention provides a method of efficiently producing a branched CD having a maltosyl group or a maltotriosyl group as bonded to the 6-hydroxyl group of the glucosyl group of CD by $\alpha$-bond, in which a liquid containing a CD and a branched oligosaccharide is treated with a debranching enzyme.

DETAILED DESCRIPTION OF THE INVENTION

The CD to be used in the present invention may any of $\alpha$-, $\beta$- and $\gamma$-CDs or may also be a mixture of them.

As the branched oligosaccharide (hereinafter referred to as "glycosyl donor") for the present invention, usable are, for example, $\alpha$-maltosyl-(1,6)-maltose (hereinafter referred to as B4) or $\alpha$-maltotriosyl-(1,6)-maltotriose (hereinafter referred to as B6) to be produced from maltose or maltotriose, respectively, by condensation reaction with a debranching enzyme, and isopanose, pullulan, a partial decomposed product of pullulan, and a mixture of them.

As the debranching enzyme for the present invention, anyone may be used which reacts with a mixture containing a branched oligosaccharide and a CD to decompose the glycosyl donor to thereby transfer the maltosyl group or maltotriosyl group to the CD by an $\alpha$-bond to give a branched CD.

The debranching enzyme to be used in the present invention is suitably selected from those which are widely distributed in the natural field. For example, there are mentioned pullulanase well known as an enzyme derived from microorganisms of the genus Klebsiella, Aerobacter aerogenes, the genus Bacillus and Enterobacter aerogenes, and isoamylase well known as an enzyme derived from microorganisms of Pseudomonas amylodelamosa.

In the reaction system of the present invention, the liquid (aqueous solution or suspension) containing a CD and a glycosyl donor is desired to have a CD concentration of approximately from 1 to 50% (w/w) and a glycosyl donor concentration of approximately from 1 to 90% (w/w). The proportion (by weight) of glycosyl donor to the CD is, though varying in accordance with the kind of the glycosyl donor to be used, suitably within the range of from 0.1/1 to 50/1, preferably from 0.3/1 to 2/1.

In carrying out the reaction of the present invention, the pH value of the reaction mixture may be from 3 to 10, preferably from 4 to 9; and the temperature thereof may be from 20° to 70° C., preferably from 30° to 60° C. The amount of the enzyme to be used in the reaction and the reaction time are closely related to each other. In general, the former may be such that the reaction may be finished in 5 to 100 hours, preferably in 5 to 20 hours, which, however, is not limitative.

Figure 1:
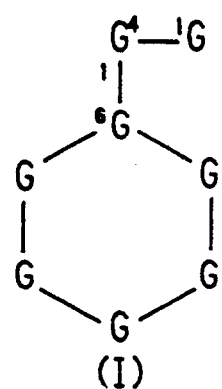
FIG. 1 shows structures of branched CDs to be obtained by the present invention, in which I indicates maltosyl-$\alpha$-CD, II indicated matotriosyl-$\alpha$-CD, III indicates maltosyl-$\beta$-CD, IV indicates maltotriosyl-$\beta$-CD, V indicates maltosyl-$\gamma$-CD and VI indicates maltotriosyl-$\gamma$-CD.
Figure 1:
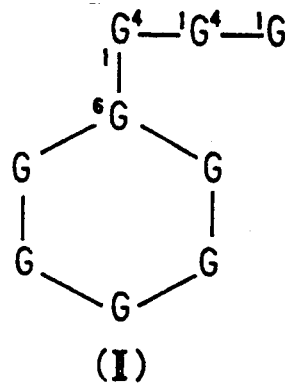
Figure 1:
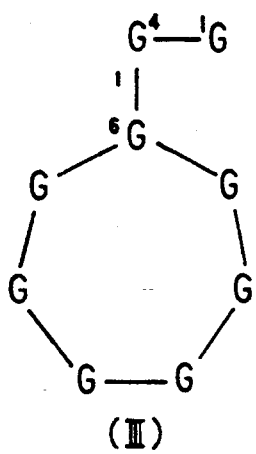
Figure 1:
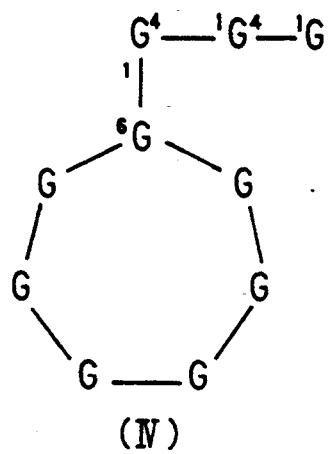
Figure 1:
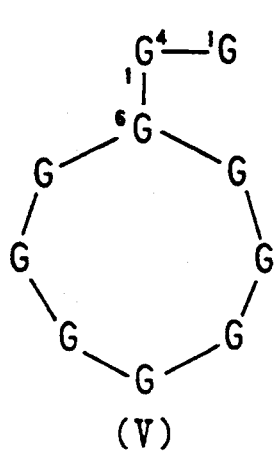
Figure 1:
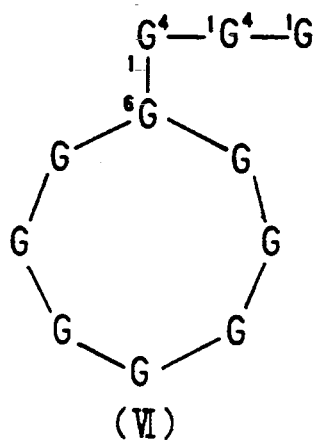

The reaction mixture as obtained by the reaction method mentioned above is subjected to high performance liquid chromatography (HPLC), whereupon the transfer product of CD is isolated. Next, the retention time in HPLC is compared with that of a standard substance and the structure of the product was analyzed by an enzymatic method. As a result, the product has been identified to be a branched CD as represented by anyone of formulae I to VI of FIG. 1.

The present invention will be explained in more detail by way of the following examples, which, however, are not intended to restrict the scope of the present invention.

EXAMPLE 1

(1) Preparation of B4

Ten g of maltose was suspended in 8.5 ml of 50 mM acetate buffer (pH 6.0), and 900 units of pullulanase derived from microorganisms of the genus *Klebsiella* (produced by Amano Pharmaceutical Co., Japan) were added thereto and reacted for 48 hours at 60° C. Regarding the enzyme activity of pullulanase, one unit thereof indicates an amount producing a reducing sugar corresponding to 1 $\mu$mol of glucose in one minute when reacted with a pullulan at a pH of 6.0 and a temperature of 40° C.

After the reaction, the reaction mixture in which the enzyme used was inactivated under heat was subjected to active charcoal chromatography and high performance liquid chromatography to isolate 2.3 g of a condensation product of B4.

(2) Production of Maltosyl-CD

Figure 2:
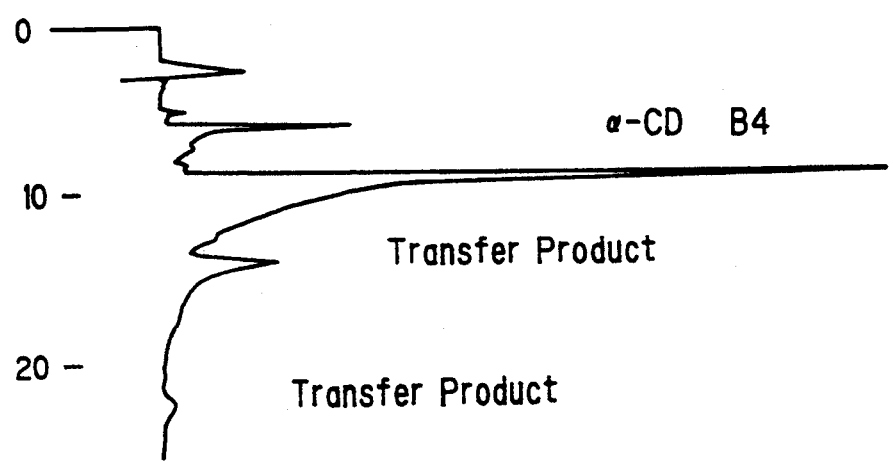
FIG. 2 shows a high performance liquid chromatograph of the reaction mixture of Example 1.

Five hundred mg of B4 as prepared in the above step (1) and 500 mg of $\alpha$-CD were dissolved in 1.25 ml of 50 mM acetate buffer (pH 6.0), and 95000 units of isoamylase derived from *Pseudomonas amylodelamosa* (produced by Hayashibara Biological and Chemical Laboratories Co., Japan) were added thereto and reacted at 40° C. for 17 hours. A part of the reaction mixture was analyzed by high performance liquid chromatography, and the analyzed result is shown in FIG. 2. One unit of isoamylase used is an amount increasing the absorbance at 610 nm by 0.1 in one hour, when reacted with a soluble glutinous rice starch at a pH of 3.5 and a temperature of 40° C.

After the reaction, the reaction mixture in which the enzyme used was inactivated under heat was subjected to high performance liquid chromatography to isolate 95 mg of a transfer product.

Figure 3:
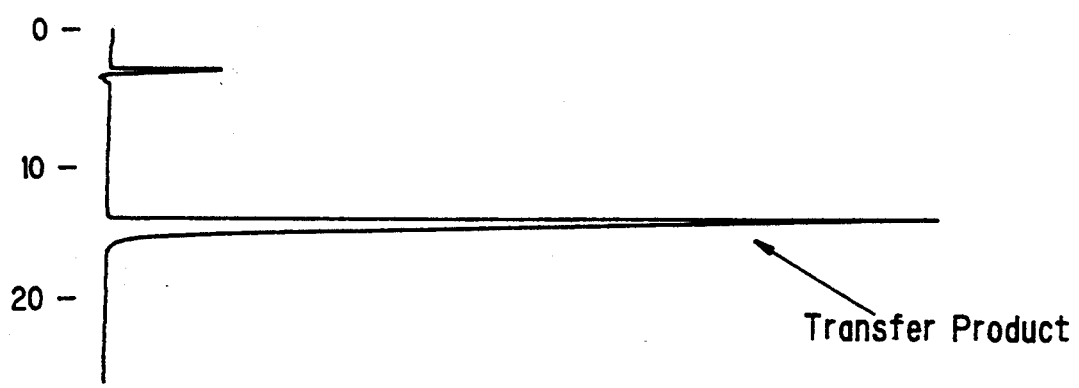
FIG. 3 shows a high performance liquid chromatograph of the transfer product of Example 1.
Figure 4:
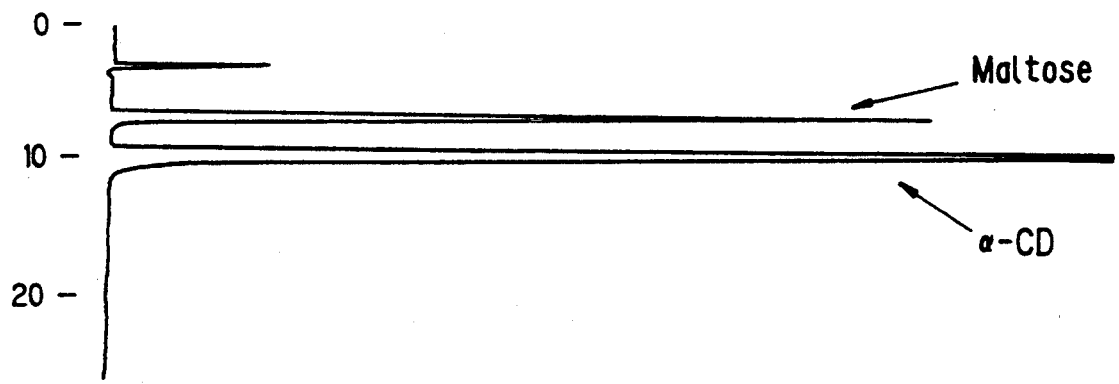
FIG. 4 shows a high performance liquid chromatograph of the hydrolyzate of the transfer product of Example 1 by isoamylase.

The transfer product was analyzed by high performance liquid chromatography (FIG. 3), in which the retention time corresponded to that of a standard substance maltosyl-$\alpha$-CD. The transfer product was completely hydrolyzed to $\alpha$-CD and maltose of the same molar amounts by isoamylase derived from *Pseudomonas amylodelamosa* (FIG. 4). From the above, the transfer product was identified to be maltosyl-$\alpha$-CD (having structural formula I of FIG. 1).

EXAMPLE 2

One g of maltose was suspended in 850 $\mu$l of 50 mM acetate buffer (pH 6.0), and 90 units of pullulanase derived from the genus Klebsiella (produced by Amano Pharmaceutical Co., Japan) were added thereto and reacted at 60° C. for 48 units. Next, 200 mg of $\alpha$-CD and 650 $\mu$l of 50 mM acetate buffer (pH 6.0) were added to the reaction mixture and reacted at 60° C. for further 8 hours.

After the reaction, the reaction liquid in which the enzyme used was inactivated under heat was subjected to high performance liquid chromatography, whereupon production of about 40 mg of maltosyl-$\alpha$-CD therein was identified.

EXAMPLE 3

(1) Preparation of B6

Ten g of maltotriose was suspended in 8.5 ml of 50 mM acetate buffer (pH 6.0), and 600 units of pullulanase derived from the genus Klebsiella (produced by Amano Pharmaceutical Co., Japan) were added thereto and reacted at 60° C. for 48 hours.

After the reaction, the reaction mixture in which the enzyme used was inactivated under heat was subjected to active charcoal chromatography and high performance liquid chromatography to isolate 2.4 g of a condensate product of B6.

(2) Production of Maltotriosyl-CD

Five hundred mg of B6 as prepared in the above step (1) and 200 mg of $\beta$-CD were dissolved in 1.25 ml of 50 mM acetic acid buffer (pH 6.0), and 50000 units of isoamylase derived from *Pseudomonas amylodelamosa* (produced by Hayashibara Biological and Chemical. Laboratories Co., Japan) were added thereto and reacted at 40° C. for 17 hours.

After the reaction, the reaction mixture in which the enzyme used was inactivated under heat was subjected to high performance liquid chromatography to isolate 45 mg of a transfer product.

Figure 5:
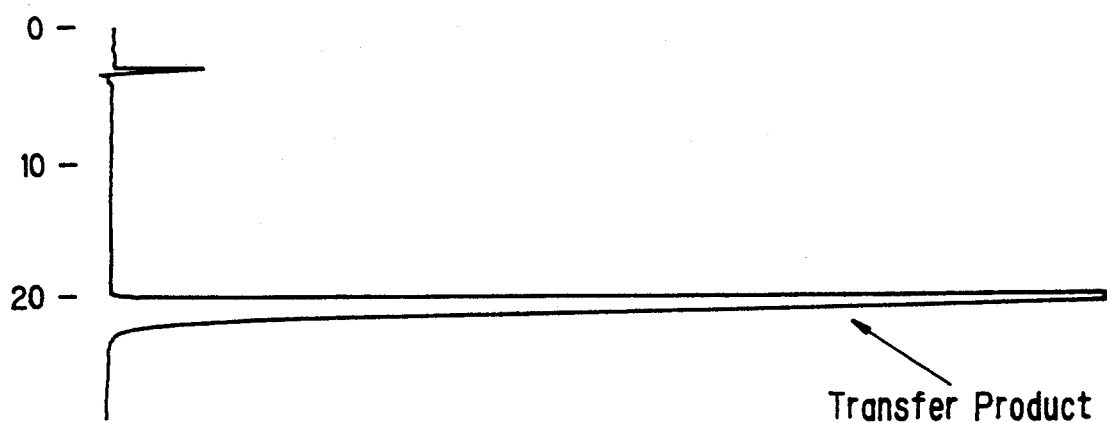
FIG. 5 shows a high performance liquid chromatograph of the transfer product of Example 3.
Figure 6:
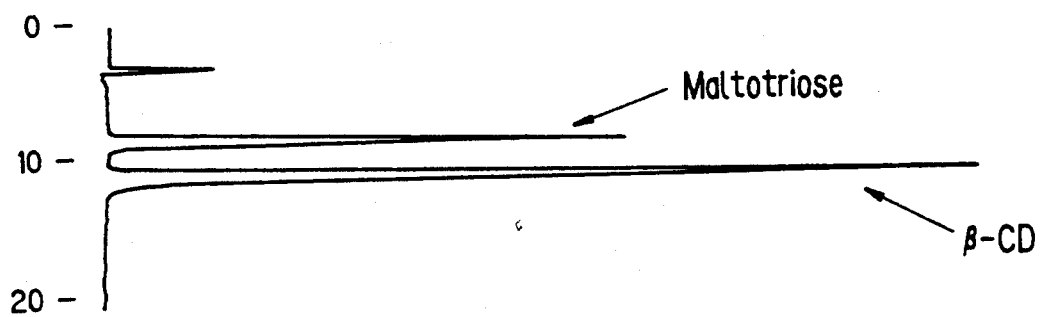
FIG. 6 is a high performance liquid chromatograph of the hydrolyzate of the transfer product of Example 3 by isoamylase.

The transfer product was analyzed by high performance liquid chromatography (FIG. 5), in which the retention time corresponded to that of a standard substance maltotriosyl-$\beta$-CD. The transfer product was completely hydrolyzed to $\beta$-CD and maltotriose of the same molar amounts by isoamylase derived from *Pseudomonas amylodelamosa* (FIG. 6). From the above, the transfer product was identified to be maltotriosyl-$\beta$-CD.

In accordance with the present invention, which has been explained in detail in the above, a branched CD having a maltosyl group or maltotriosyl group as bonded to the glucose of a CD molecule via an $\alpha$-1,6 bond is obtained by transglycosylation of a debranching enzyme. In particular, a branched CD having only one molecule of maltosyl or maltotriosyl group as bonded thereto is obtained especially efficiently.

While the invention has been described in detail and with reference to specific embodiments thereof, it will be apparent to one skilled in the art that various changes and modifications can be made therein without departing from the spirit and scope thereof.

What is claimed is:

1. A method of producing a branched cyclodextrin, which comprises reacting a liquid containing a cyclodextrin and a branched oligosaccharide selected from the group consisting of α-maltosyl-(1,6)-maltose, α-maltotriosyl-(1,6)-maltotriose, isopanose, pullulan, a partial decomposed product of pullulan, and a mixture thereof with a debranching enzyme.

2. The method of producing a branched cyclodextrin as claimed in claim 1, wherein the branched cyclodextrin is α-maltosyl-(1,6)-cyclodextrin or α-maltotriosyl-(1,6)-cyclodextrin.

3. The method of producing a branched cyclodextrin as claimed in claim 1, wherein the debranching enzyme is pullulanase or isoamylase derived from microorganisms.

4. The method of producing a branched cyclodextrin as claimed in claim 1, wherein the cyclodextrin is in a concentration of 1 to 50% (w/w) and the branched oligosaccharide is in a concentration of 1 of 90% (w/w).

5. The method of producing cyclodextrin as claimed in claim 1, wherein the reaction of the liquid and the debranching enzyme is carried out at a pH value of 3 to 10 and a temperature of 20° to 70° C.

6. The method of producing a branched cyclodextrin as claimed in claim 2, wherein the debranching enzyme is pullulanase or isoamylase derived from microorganisms; the cyclodextrin is in a concentration of 1 to 50% (w/w); the branched oligosaccharide is in a concentration of 1 to 90% (w/w) and the reaction of the liquid and the debranching enzyme is carried out at a pH value of 3 to 10 and a temperature of 20° to 70° C.

7. The method of producing a branched cyclodextrin as claimed in claim 6, wherein the debranching enzyme is pullulanase which is derived from a microorganism of a genus selected from the group consisting of *Klebsiella, Aerobacter aerogenes, Bacillus* and *Enterobacter aerogenes.*

8. The method of producing a branched cyclodextrin as claimed in claim 6, wherein the debranching enzyme is isoamylase which is derived from *Pseudomonas amlodelamose.*

9. The method of producing a branched cyclodextrin as claimed in claim 6 wherein the proportion by weight of the branched oligosaccharide to the cyclodextrin is 0.1/1 to 50/1.

10. The method of producing a branched cyclodextrin as claimed in claim 9, wherein the proportion by weight of the branched oligosaccharide to the cyclodextrin is 0.3/1 to 2/1.

11. The method of producing a branched cyclodextrin as claimed in claim 10, wherein the pH is 4 to 9, the temperature is 30° to 60° C. and the reaction is carried out for 5 to 20 hours.

* * * * *